(12) United States Patent
Nishimura et al.

(10) Patent No.: US 11,048,951 B2
(45) Date of Patent: Jun. 29, 2021

(54) OCCUPANT STATE RECOGNITION APPARATUS

(71) Applicant: TOYOTA JIDOSHA KABUSHIKI KAISHA, Toyota (JP)

(72) Inventors: Naoki Nishimura, Nagoya (JP); Shunichiroh Sawai, Numazu (JP); Kenichiroh Hara, Yokohama (JP); Koichiro Yamauchi, Sunto-gun (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 38 days.

(21) Appl. No.: 16/456,784

(22) Filed: Jun. 28, 2019

(65) Prior Publication Data

US 2020/0026938 A1 Jan. 23, 2020

(30) Foreign Application Priority Data

Jul. 23, 2018 (JP) .............................. JP2018-137788

(51) Int. Cl.
*G06K 9/00* (2006.01)
*A61B 3/10* (2006.01)
*A61B 5/18* (2006.01)

(52) U.S. Cl.
CPC ............ *G06K 9/00845* (2013.01); *A61B 3/10* (2013.01); *A61B 5/18* (2013.01); *G06K 9/0061* (2013.01)

(58) Field of Classification Search
CPC .... G06K 9/00845; G06K 9/0061; A61B 3/10; A61B 5/18
See application file for complete search history.

(56) References Cited

U.S. PATENT DOCUMENTS

| 7,202,793 | B2* | 4/2007 | Grace | A61B 5/1103 340/576 |
| 7,253,739 | B2* | 8/2007 | Hammoud | A61B 5/1103 340/573.1 |
| 8,139,819 | B2* | 3/2012 | Morita | G08B 29/26 382/103 |
| 8,538,091 | B2* | 9/2013 | Kaneda | G06K 9/00845 382/118 |
| 8,891,824 | B2* | 11/2014 | Wu | A61B 5/18 382/103 |

(Continued)

FOREIGN PATENT DOCUMENTS

JP 5871290 B2 3/2016

*Primary Examiner* — Gregory M Desire
(74) *Attorney, Agent, or Firm* — Sughrue Mion, PLLC (57) ABSTRACT

An occupant state recognition apparatus including an eyelid opening recognition unit configured to recognize an eyelid opening of a driver and maximum and minimum values of the eyelid opening; an eye state determination unit configured to determine that the eye is in an eye open state if the eyelid opening becomes greater than or equal to a preset threshold value, and to determine that the eye is in an eye closed state if the eyelid opening becomes less than the threshold value; and a threshold value resetting unit configured to reset the threshold value to a value between the maximum value and the minimum value of the eyelid opening, if the maximum value (or the minimum value) has not become greater (or less) than or equal to the threshold value for a predetermined period or a period corresponding to a predetermined number of times of eyelid opening and closing.

4 Claims, 9 Drawing Sheets

(56) References Cited

U.S. PATENT DOCUMENTS

| | | | |
|---|---|---|---|
| 10,095,936 B2* | 10/2018 | Ohya | G06K 9/0061 |
| 10,395,510 B2* | 8/2019 | Du | G02B 27/017 |
| 2020/0026938 A1* | 1/2020 | Nishimura | A61B 3/14 |

* cited by examiner

OCCUPANT STATE RECOGNITION APPARATUS

CROSS-REFERENCE TO RELATED APPLICATION

This application claims the benefit of priority from Japanese Patent Application No. 2018-137788, filed on Jul. 23, 2018, the entire contents of which are incorporated herein by reference.

TECHNICAL FIELD

The present disclosure relates to an occupant state recognition apparatus.

BACKGROUND

In the related art, as a technique related to an occupant state recognition apparatus, there is a communication system for communication using a blink of an eye of a subject (for example, Japanese Patent No. 5871290). In the communication system, a plurality of frame images, that is, images of an eye of the subject continuously captured in time series, are used to determine a blink of the eye of the subject. If a region indicative of the eye of the subject on the plurality of frame images decreases, eye closing is determined to have occurred. If the region on the plurality of frame images increases from when the eye closing is determined, eye opening is determined to have occurred.

SUMMARY

In a technique to recognize a state of an occupant by determining whether the eye is in an eye open state or an eye closed state, when based on an eyelid opening and an opening threshold value, due to individual differences in the degree of opening and closing of an eyelid, the eye open state may be a half-eye state or the eye closed state may be a half-eye state. Therefore, it is desirable to properly recognize the state of the occupant by determining whether the eye is in the eye open state or the eye closed state while taking account of the individual differences.

In the technical field, it is desirable to properly recognize a state of an occupant by determining whether an eye is in an eye open state or an eye closed state while taking account of individual differences.

According to an aspect of the present disclosure, there is provided an occupant state recognition apparatus that recognizes a state of an occupant by determining an eye open state and an eye closed state of an eye of a driver sitting in a driver's seat of a vehicle, the apparatus including an eyelid opening recognition unit configured to recognize an eyelid opening of the driver, a maximum value of the eyelid opening of the driver, and a minimum value of the eyelid opening of the driver based on image information captured by a driver monitoring camera of the vehicle; an eye state determination unit configured to determine that the eye is in the eye open state if the eyelid opening becomes greater than or equal to a threshold value which is preset, and to determine that the eye is in the eye closed state if the eyelid opening becomes less than the threshold value; and a threshold value resetting unit configured to reset the threshold value to a value between the maximum value and the minimum value of the eyelid opening of the driver recognized by the eyelid opening recognition unit, if the maximum value has not become greater than or equal to the threshold value for a predetermined period or a period corresponding to a predetermined number of times of eyelid opening and closing, or if the minimum value has not become less than or equal to the threshold value for the predetermined period or the period corresponding to the predetermined number of times of eyelid opening and closing.

In the occupant state recognition apparatus according to the aspect of the present disclosure, the threshold value resetting unit resets the threshold value to the value between the maximum value and the minimum value of the eyelid opening of the driver recognized by the eyelid opening recognition unit, if the maximum value of the eyelid opening has not become greater than or equal to the threshold value for the predetermined period or the period corresponding to the predetermined number of times of eyelid opening and closing (in other words, if the eye open state has become a half-eye state), or if the minimum value of the eyelid opening has not become less than or equal to the threshold value for the predetermined period or the period corresponding to the predetermined number of times of eyelid opening and closing (in other words, if the eye closed state has become the half-eye state). The eye state determination unit can determine whether the eye is in the eye open state or the eye closed state because the threshold value is reset to the value between the maximum value and the minimum value of the eyelid opening of the driver. Therefore, the occupant state recognition apparatus can properly recognize the state of the occupant by determining whether the eye is in the eye open state or the eye closed state while taking account of individual differences.

In the occupant state recognition apparatus of the embodiment, the threshold value resetting unit may be configured to determine whether there has been a driver replacement, and to reset the threshold value to the value between the maximum value and the minimum value of the eyelid opening of the driver recognized by the eyelid opening recognition unit, if the threshold value resetting unit determined that there has been the driver replacement. In this case, the eye state determination unit can certainly determine whether an eye is in the eye open state or the eye closed state because the threshold value is reset in association with the replacement, even though, for example, there are individual differences in the degree of eyelid opening and closing between the driver before the replacement and another driver after the replacement.

As described above, according to various aspects or the embodiment of the present disclosure, it is possible to properly recognize the state of the occupant by determining whether the eye is in the eye open state or the eye closed state while taking account of the individual differences.

DETAILED DESCRIPTION

Hereinbelow, an embodiment of the present disclosure will be described with reference to the drawings.

Figure 1:
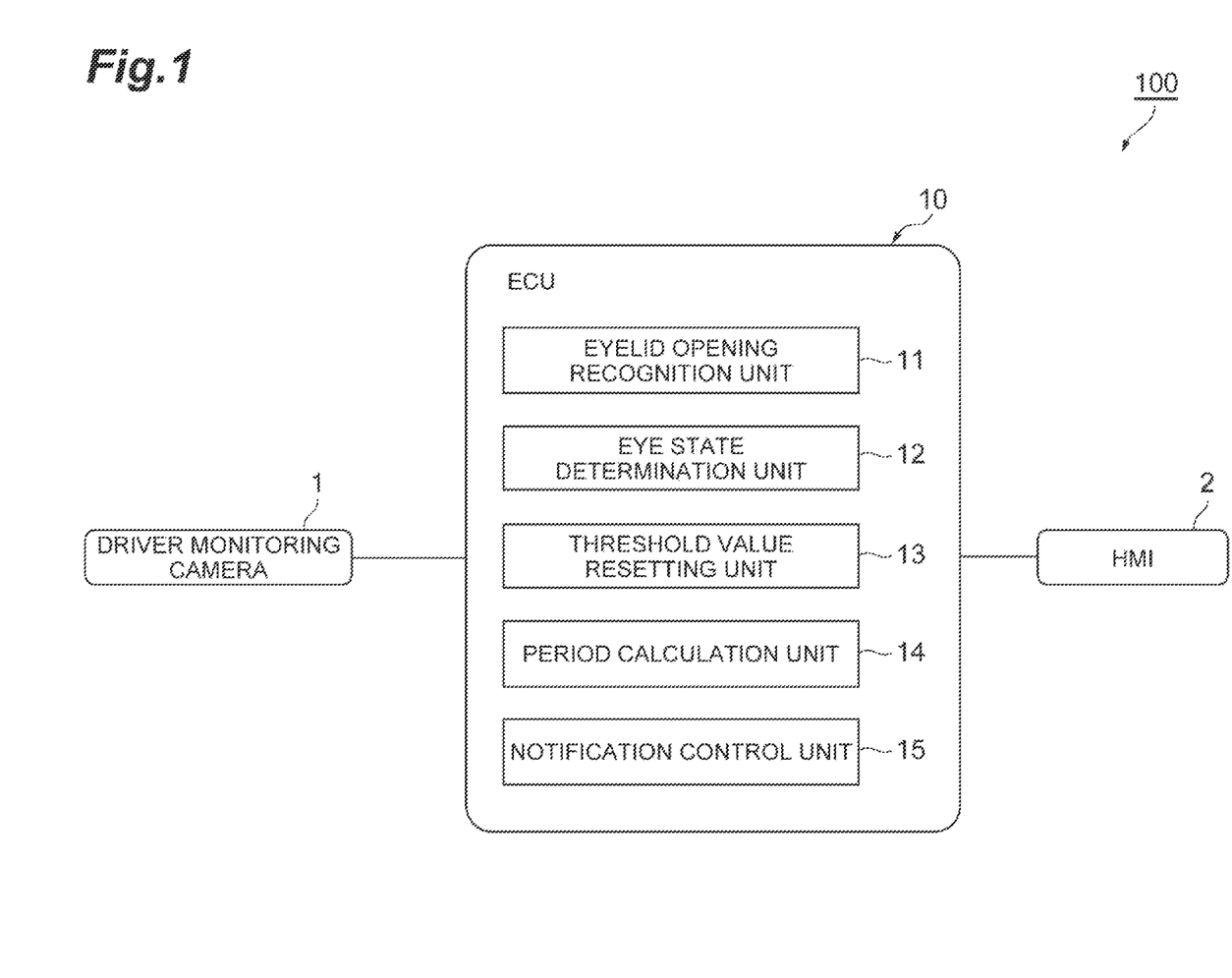
FIG. 1 is a block diagram illustrating an occupant state recognition apparatus of an embodiment.

FIG. 1 is a block diagram illustrating an occupant state recognition apparatus of the embodiment. As illustrated in FIG. 1, an occupant state recognition apparatus 100 recognizes a state of a driver (state of an occupant) by estimating an eye open period and an eye closed period of an eye of the driver sitting in a driver's seat of a vehicle. The occupant state recognition apparatus 100 notifies the driver via voice or the like, for example, if it is determined that an alertness of the driver is diminishing, when based on at least one of the eye open period and the eye closed period.

Configuration of Occupant State Recognition Apparatus 100

As illustrated in FIG. 1, the occupant state recognition apparatus 100 includes an electronic control unit (ECU) 10. The ECU 10 is an electronic control unit having a central processing unit (CPU), a read only memory (ROM), a random access memory (RAM), and a controller area network (CAN) communication circuit. The ECU 10 realizes various functions by uploading a program stored in the ROM onto the RAM, and executing the program loaded onto the RAM via the CPU. The ECU 10 may be configured to include a plurality of electronic units.

The ECU 10 is connected to a driver monitoring camera 1 and a human machine interface (HMI) 2.

The driver monitoring camera 1 is provided on a cover of a steering column of the vehicle at a position in front of the driver, for example, and captures images of the driver. A plurality of the driver monitoring cameras 1 may be provided to capture images of the driver in a plurality of directions. The driver monitoring camera 1 transmits captured image information of the driver to the ECU 10.

The HMI 2 is an on-board interface for exchanging information between the occupant state recognition apparatus 100 and the driver. The HMI 2 includes a speaker capable of outputting a voice message. The HMI 2 outputs a voice message via the speaker in response to a control signal from the ECU 10.

Subsequently, a functional configuration of the ECU 10 will be described. The ECU 10 has an eyelid opening recognition unit 11; an eye state determination unit 12; a threshold value resetting unit 13; a period calculation unit 14; and a notification control unit 15. A sever capable of communicating with a vehicle V may execute part of functions of the ECU 10 which will be described hereinbelow.

The eyelid opening recognition unit 11 recognizes an eyelid opening of the driver based on the image information captured by the driver monitoring camera 1. The eyelid opening is an index representing the degree of opening of an eyelid. The eyelid opening can be denoted by an eyelid distance ratio, for example. The eyelid distance ratio represents the ratio of an eyelid distance calculated by the eyelid opening recognition unit 11 to a denominator eyelid distance which is the denominator of the eyelid distance ratio. The denominator eyelid distance is not a maximum value of the eyelid opening of the driver, but a preset eyelid distance. The denominator eyelid distance can be denoted by a maximum value of an eyelid opening in an eyelid opening distribution acquired in advance from a pretest administered for a plurality of subjects as targets, for example.

The eyelid opening recognition unit 11 calculates an eyelid distance between an upper eyelid and a lower eyelid based on the image captured by the driver monitoring camera 1. The eyelid opening recognition unit 11 calculates a 3-D distance from the upper eyelid to the lower eyelid as the eyelid distance, for example. The 3-D distance from the upper eyelid to the lower eyelid is equivalent to the length of a line segment connecting a center portion of the upper eyelid and a center portion of the lower eyelid in a 3-D facial model. The eyelid opening recognition unit 11 can calculate the 3-D distance by a well-known technique. For example, the eyelid opening recognition unit 11 sets feature points for an eye inner corner and an eye outer corner on an image of the eye of the driver which is captured by the driver monitoring camera 1, and recognizes the upper eyelid and the lower eyelid in the 3-D facial model by image analysis such as pattern matching using the feature points. The eyelid opening recognition unit 11 calculates the length of the line segment connecting the center portion of the upper eyelid and the center portion of the lower eyelid in the recognized 3-D facial model, and recognizes the calculated length as the eyelid distance.

The eyelid opening recognition unit 11 recognizes the eyelid opening by dividing the calculated eyelid distance by the denominator eyelid distance. For example, the eyelid opening is denoted in percentage, and if the calculated eyelid distance is 0% (if the eyelid is fully closed), the eyelid opening becomes zero. If the calculated eyelid distance is equal to a maximum eyelid distance (if the eyelid is fully open), the eyelid opening becomes 100%. The eyelid opening may be denoted as a ratio value in a range of 0 to 1.

The eyelid opening recognition unit 11 recognizes a maximum value of the eyelid opening of the driver and a minimum value of the eyelid opening of the driver based on the calculated eyelid distance. The eyelid opening recognition unit 11 recognizes the maximum value of the eyelid opening based on a maximum eyelid distance obtained among eyelid distances calculated in a predetermined acquisition period in a process of resetting an opening threshold value which will be described later, for example. The eyelid opening recognition unit 11 recognizes the minimum value of the eyelid opening based on a minimum eyelid distance obtained among the eyelid distances calculated in the predetermined acquisition period in the process of resetting the opening threshold value, for example.

The eye state determination unit 12 determines a state of the eye of the driver based on the eyelid opening recognized by the eyelid opening recognition unit 11. The state of the eye of the driver includes an eye open state and an eye closed state.

The eye open state represents a state where the eyelid is open to a predetermined opening or greater due to an eye blink of the driver. The eye open state may not necessarily be a state where the eyelid is fully open. The eye open state may be a half-eye state. The "eyelid fully open state" represents a state where the eyelid opening reaches a maximum value of the eyelid opening in the eyelid opening distribution acquired in advance from the pretest administered for the plurality of subjects as targets, for example.

The eye closed state represents a state where the eyelid opening is less than the predetermined opening due to an eye blink of the driver or a diminishing in the alertness of the driver. The eye closed state may not necessarily be a state where the eyelid is fully closed. The eye closed state may be the half-eye state. The "eyelid fully closed state" represents a state where the eyelid opening reaches a minimum value of the eyelid opening in the eyelid opening distribution acquired in advance from the pretest administered for the plurality of subjects as targets, for example.

Specifically, the eye state determination unit 12 determines that the eye is in the eye open state, if the eyelid opening recognized by the eyelid opening recognition unit 11 is greater than or equal to the opening threshold value (threshold value). The eye state determination unit 12 determines that the eye is in the eye closed state, if the eyelid opening recognized by the eyelid opening recognition unit 11 is less than the opening threshold value. The eye state determination unit 12 may store a determination result for the state (eye open state or eye closed state) of the eye of the driver, and a determination time associated with the determination result. The eye state determination unit 12 may store the determination result as time series of flag information.

The opening threshold value is a threshold value of the eyelid opening for determining the eye open state or the eye closed state. For example, in an initial process executed by the eye state determination unit 12 after the ECU 10 wakes up, an initial opening threshold value which is preset is used as the opening threshold value. The initial opening threshold value can be preset based on the eyelid opening distribution acquired in advance from the pretest for the plurality of subjects as targets, for example. The initial opening threshold value may be stored in the ECU 10 in advance.

The opening threshold value can be reset by the threshold value resetting unit 13 which will be described later. When the opening threshold value is reset by the threshold value resetting unit 13, the eye state determination unit 12 determines that the eye is in the eye open state, if the eyelid opening recognized by the eyelid opening recognition unit 11 is greater than or equal to the reset opening threshold value. The eye state determination unit 12 determines that the eye is in the eye closed state, if the eyelid opening recognized by the eyelid opening recognition unit 11 is less than the reset opening threshold value.

As a first threshold value resetting, for example, if a predetermined threshold value reset condition is satisfied, the threshold value resetting unit 13 resets the opening threshold value to a value between the maximum value and the minimum value of the eyelid opening of the driver recognized by the eyelid opening recognition unit 11. For example, the predetermined threshold value reset condition may indicate a condition where the maximum value of the eyelid opening has not become greater than or equal to the opening threshold value for a predetermined period or a period corresponding to a predetermined number of times of eyelid opening and closing. Alternatively, the predetermined threshold value reset condition may indicate a condition where the minimum value of the eyelid opening has not become less than or equal to the opening threshold value for the predetermined period or the period corresponding to the predetermined number of times of eyelid opening and closing (detailed description will be given later).

As a second threshold value resetting, for example, the threshold value resetting unit 13 determines whether there has been a driver replacement. The threshold value resetting unit 13 resets the opening threshold value to a value between the maximum value and the minimum value of the eyelid opening of the driver recognized by the eyelid opening recognition unit 11, if the threshold value resetting unit 13 determined that there has been the driver replacement (detailed description will be given later).

The period calculation unit 14 calculates the eye open period which is a period it takes for the state of the eye to be changed from the eye open state to the eye closed state, based on a determination result output from the eye state determination unit 12. The eye open period represents a period for which the eyelid is continuously open to the predetermined opening or greater due to an eye blink of the driver. A start time of the eye open period is the determination time that the eye of the driver has been determined to enter the eye open state. Specifically, the start time of the eye open period can be the determination time that the determination result output from the eye state determination unit 12 has been changed from the eye closed state to the eye open state. An end time of the eye open period is the determination time that the eye of the driver has been determined to enter the eye closed state. Specifically, the end time of the eye open period can be the determination time that the determination result output from the eye state determination unit 12 has been changed from the eye open state to the eye closed state after the start time of the eye open period.

The notification control unit 15 controls a notification to the driver based on a calculation result output from the period calculation unit 14. The notification control unit 15 calculates a time interval of blinks based on the eye open period calculated by the period calculation unit 14, for example. The notification control unit 15 determines that the alertness of the driver is diminishing, if the time interval of blinks is less than a predetermined blink interval threshold value. The notification control unit 15 encourages the driver to take a rest by notifying the driver of a voice message such as "are you tired?", if the notification control unit 15 determined that the alertness of the driver is diminishing.

First Threshold Value Resetting

Subsequently, a first threshold value resetting operation and a first threshold value resetting process executed by the threshold value resetting unit 13 will be described with reference to FIGS. 2 to 6.

Figure 2:
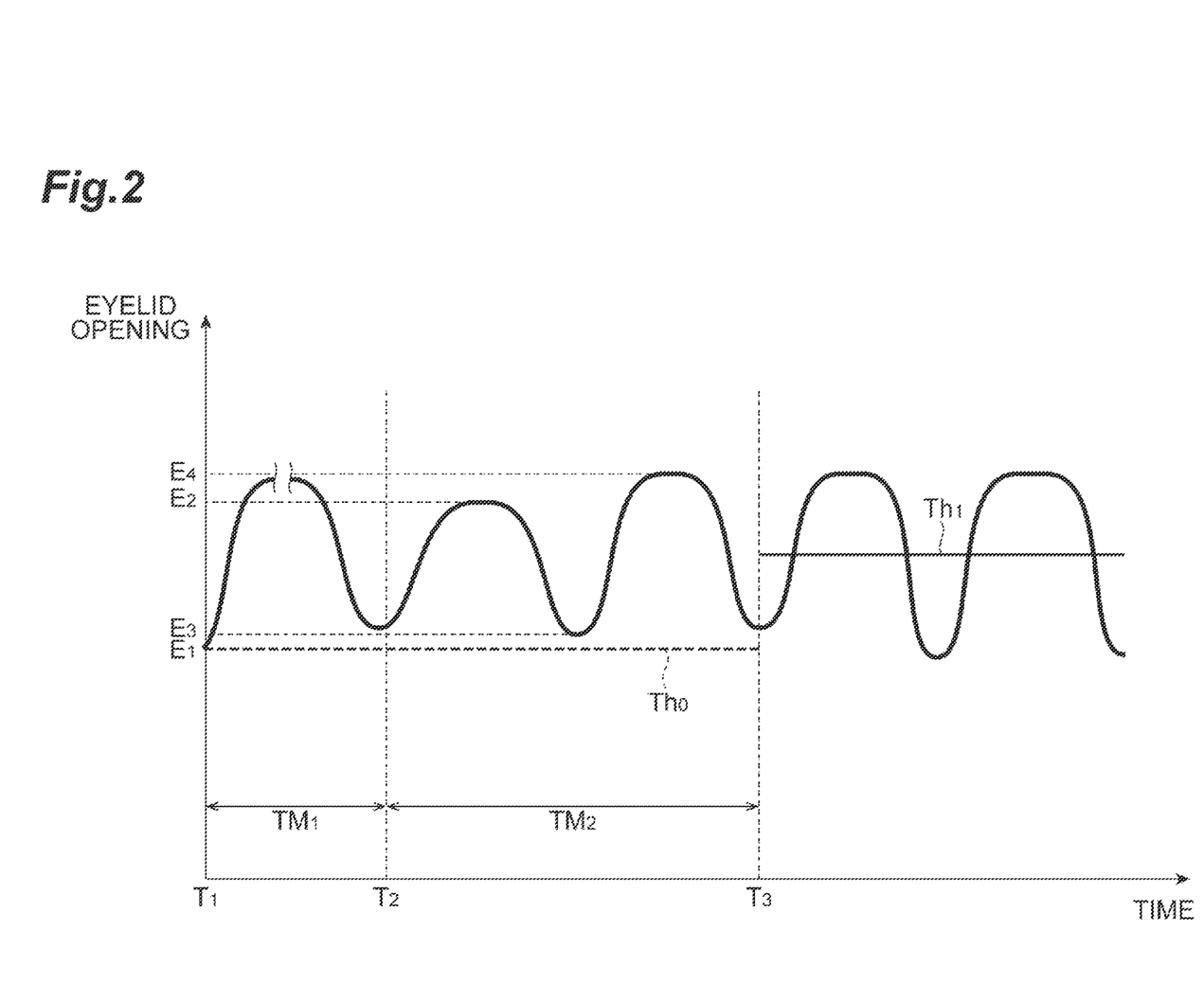
FIG. 2 is a timing chart illustrating an example of a first threshold value resetting.

FIG. 2 is a timing chart illustrating an example of an operation of the occupant state recognition apparatus. In FIG. 2, the horizontal axis represents time. In FIG. 2, the vertical axis represents the eyelid opening. In FIG. 2, the solid line represents a change over time in the eyelid opening of the driver. As an example, FIG. 2 illustrates a case where the eye closed state becomes the half-eye state when the threshold value resetting unit 13 determined that there has been no driver replacement described later.

In FIG. 2, a time $T_1$ indicates the time that an eyelid opening $E_1$ becomes equal to an opening threshold value $Th_0$. The opening threshold value $Th_0$ is not limited to a specific threshold value, and is an initial opening threshold value which is preset, for example. A time $T_2$ indicates the time that a period $TM_1$ (predetermined period) has elapsed from the time $T_1$. A start time of the period $TM_1$ can indicate the time that the eyelid opening has finally become equal to the opening threshold value $Th_0$, for example.

In the period from the time $T_1$ to the time $T_2$, the eyelid opening is greater than the opening threshold value $Th_0$, which is not illustrated in detail in FIG. 2. That is, the minimum value of the eyelid opening has not become less than or equal to the opening threshold value $Th_0$ in the period from the time $T_1$ to the time $T_2$. In this case, the threshold value resetting unit 13 resets the opening threshold value to a value between the maximum value and the minimum value of the eyelid opening of the driver recognized by the eyelid opening recognition unit 11.

A time $T_3$ indicates the time that a period $TM_2$ (acquisition period) has elapsed from the time $T_2$. The acquisition period indicates a period of recognizing the maximum value and the minimum value of the eyelid opening of the driver for resetting the opening threshold value. The acquisition period may be preset to a period for which the driver can blink multiple times. The acquisition period is not limited to a specific period, and can be set to 150 seconds, for example.

In the acquisition period from the time $T_2$ to the time $T_3$, the eyelid opening recognition unit 11 recognizes the maximum value and the minimum value of the eyelid opening of the driver. In the example illustrated in FIG. 2, firstly, the eyelid opening recognition unit 11 recognizes an eyelid opening $E_2$ as the maximum value of the eyelid opening of the driver in the period from the time $T_2$ to the time $T_3$. Subsequently, the eyelid opening recognition unit 11 recognizes an eyelid opening $E_3$ as the minimum value of the eyelid opening of the driver. Subsequently, the eyelid opening recognition unit 11 recognizes an eyelid opening $E_4$ as a new maximum value of the eyelid opening of the driver.

At the time $T_3$, the threshold value resetting unit 13 resets an opening threshold value $Th_1$ to a value between the eyelid opening $E_4$ recognized as the maximum value of the eyelid opening of the driver and the eyelid opening $E_3$ recognized as the minimum value of the eyelid opening of the driver. Herein, the threshold value resetting unit 13 calculates a median value between the maximum value and the minimum value of the eyelid opening of the driver recognized by the eyelid opening recognition unit 11, as the reset opening threshold value. In FIG. 2, as an example, the threshold value resetting unit 13 calculates a median value between the maximum value (eyelid opening $E_4$) and the minimum value (eyelid opening $E_3$), and resets the opening threshold value $Th_1$ to the median value. Therefore, after the time $T_3$, the eye state determination unit 12 can determine whether the eye is in the eye open state or the eye closed state.

Consecutively, the threshold value resetting unit 13 resets the opening threshold value to a value between the maximum value and the minimum value of the eyelid opening of the driver recognized by the eyelid opening recognition unit 11, if the minimum value of the eyelid opening has not become less than or equal to the opening threshold value for the period corresponding to the predetermined number of times of eyelid opening and closing.

Figure 3:
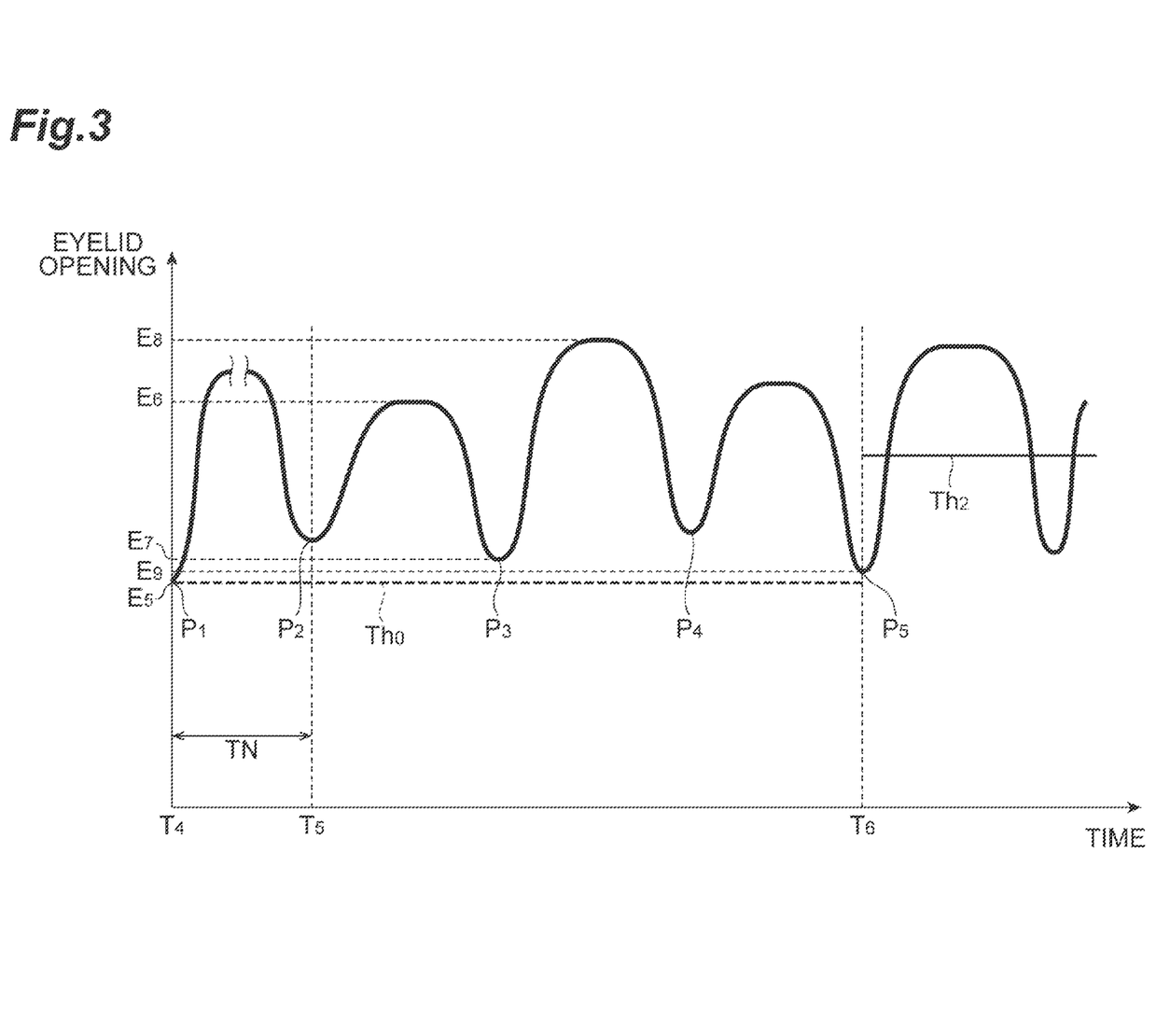
FIG. 3 is another timing chart illustrating an example of the first threshold value resetting.

FIG. 3 is a timing chart illustrating another example of the operation of the occupant state recognition apparatus. The horizontal axis and the vertical axis of FIG. 3 represents the same parameters as the horizontal axis and the vertical axis of FIG. 2. Similar to FIG. 2, FIG. 3 illustrates a case where the eye closed state becomes the half-eye state when the threshold value resetting unit 13 determined that there has been no driver replacement described later.

In FIG. 3, a time $T_4$ indicates a time corresponding to a point $P_1$ on the solid line, at which an eyelid opening $E_5$ is equal to the opening threshold value $Th_0$. A period TN is equivalent to the period corresponding to the predetermined number of times of eyelid opening and closing. The period TN indicates a period from the time $T_4$ to a time $T_5$ corresponding to a point P2 on the solid line, for which the driver has blinked the predetermined number of times of eyelid opening and closing. A start time of the period TN represents the time that the accumulation of the number of times of eyelid opening and closing starts. The start time of the period TN can indicate the time that the eyelid opening has finally become equal to the opening threshold value $Th_0$, for example. The number of times of eyelid opening and closing indicates the number of times that the eyelid is open and closed due to eye blinks of the driver without the eyelid opening crossing the opening threshold value $Th_0$. The number of times of eyelid opening and closing may increase at timings (a point $P_3$, a point $P_4$, and a point $P_5$ on the solid line) that the eyelid opening turns from decreasing to increasing while remaining greater than the opening threshold value $Th_0$.

In the period from the time $T_4$ to the time $T_5$, the driver has blinked the predetermined number of times of eyelid opening and closing while remaining greater than the opening threshold value $Th_0$, which is not illustrated in detail in FIG. 3. That is, the minimum value of the eyelid opening has not become less than or equal to the opening threshold value $Th_0$ in the period TN equivalent to the period corresponding to the predetermined number of times of eyelid opening and closing. In this case, the threshold value resetting unit 13 resets the opening threshold value to a value between the maximum value and the minimum value of the eyelid opening of the driver recognized by the eyelid opening recognition unit 11.

A time $T_6$ is equivalent to an end time of an acquisition period starting from the time $T_5$. The time $T_6$ indicates the time that the driver has blinked a predetermined acquired number of times of eyelid opening and closing after the time $T_5$. The acquired number of times of eyelid opening and closing indicates the number of times of eyelid opening and closing required to recognize the maximum value and the minimum value of the eyelid opening of the driver for resetting the opening threshold value. The acquired number of times of eyelid opening and closing may be preset to the number of times corresponding to a plurality of blinks done by the driver. In the example illustrated in FIG. 3, for illustrative purposes, the acquired number of times of eyelid opening and closing is three (the point $P_3$, the point $P_4$, and the point $P_5$ on the solid line). The acquired number of times of eyelid opening and closing is not particularly limited to the example illustrated in FIG. 3.

The eyelid opening recognition unit 11 recognizes the maximum value and the minimum value of the eyelid opening of the driver in the acquisition period from the time $T_5$ to the time $T_6$, for which the driver has blinked the predetermined acquired number of times of eyelid opening and closing. In the example illustrated in FIG. 3, firstly, the eyelid opening recognition unit 11 recognizes an eyelid opening $E_6$ as the maximum value of the eyelid opening of the driver in the period from the time $T_5$ to the time $T_6$. Subsequently, the eyelid opening recognition unit 11 recognizes an eyelid opening $E_7$ as the minimum value of the eyelid opening of the driver. Subsequently, the eyelid opening recognition unit 11 recognizes an eyelid opening $E_8$ as a new maximum value of the eyelid opening of the driver. Subsequently, the eyelid opening recognition unit 11 recognizes an eyelid opening $E_9$ as a new minimum value of the eyelid opening of the driver.

At the time $T_6$, the threshold value resetting unit 13 resets an opening threshold value $Th_2$ to a value between the eyelid opening $E_8$ recognized as the maximum value of the eyelid opening of the driver and the eyelid opening $E_9$ recognized as the minimum value of the eyelid opening of the driver. In FIG. 3, as an example, the threshold value resetting unit 13 calculates a median value between the maximum value (eyelid opening $E_8$) and the minimum value (eyelid opening $E_9$), and resets the opening threshold value $Th_2$ to the median value. Therefore, after the time $T_6$, the eye state determination unit 12 can determine whether the eye is in the eye open state or the eye closed state.

Figure 4:
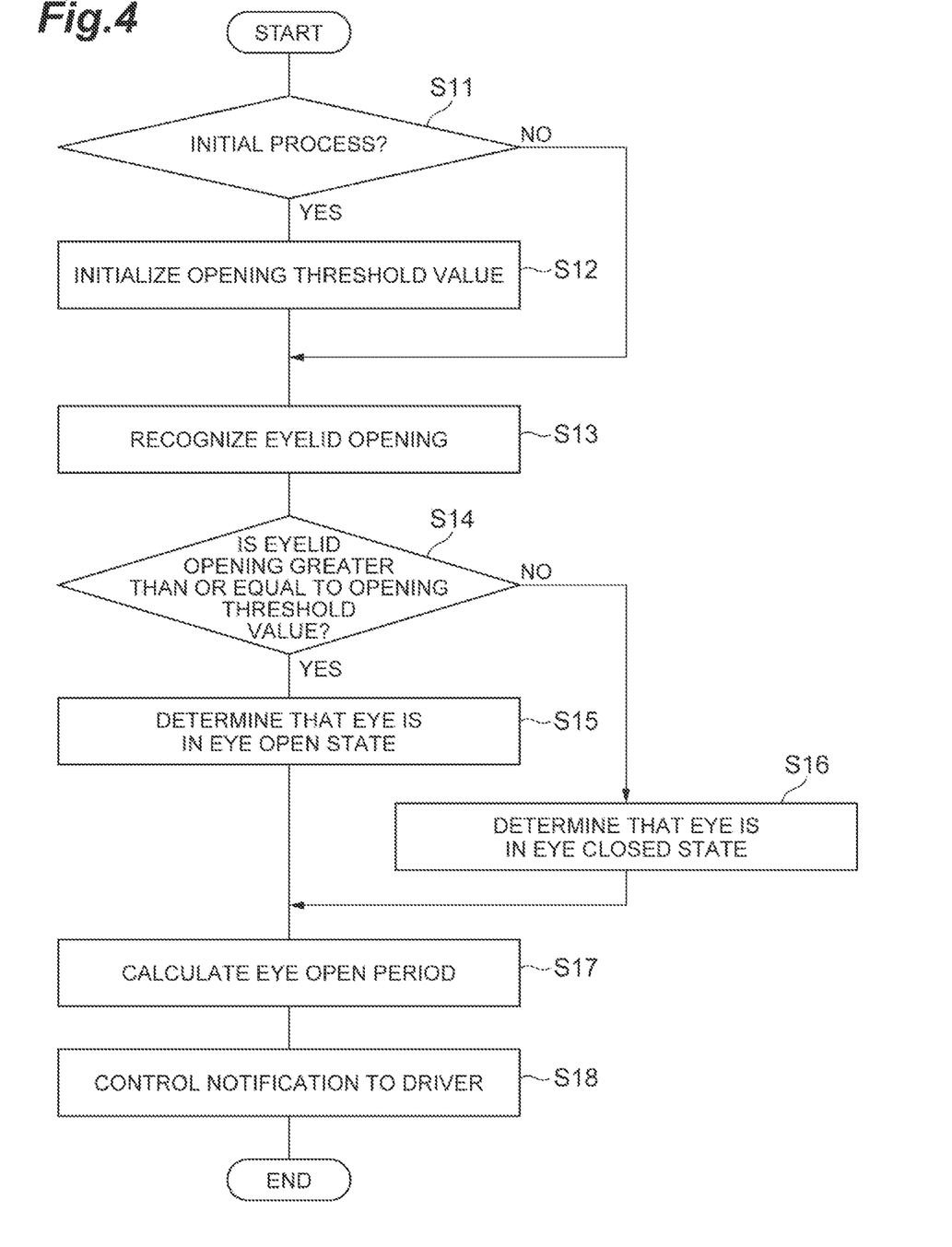
FIG. 4 is a flowchart illustrating a process executed by the occupant state recognition apparatus.

Subsequently, an example of a computational process executed by the occupant state recognition apparatus 100 will be described. FIG. 4 is a flowchart illustrating the process executed by the occupant state recognition apparatus 100. The process of the flowchart illustrated in FIG. 4 is executed when a power source of the ECU 10 is turned on, for example, also including when a vehicle including the occupant state recognition apparatus 100 travels.

In S11, the ECU 10 of the occupant state recognition apparatus 100 causes the eye state determination unit 12 to determine whether the process of the ECU 10 is an initial process. If it is determined that the process of the ECU 10 is the initial process (S11: YES), the eye state determination unit 12 initializes an opening threshold value in S12. If it is determined that the process of the ECU 10 is not the initial process (S11: NO), the eye state determination unit 12 does not initialize the opening threshold value.

In S13, the ECU 10 causes the eyelid opening recognition unit 11 to recognize an eyelid opening. The eyelid opening recognition unit 11 recognizes the eyelid opening based on image information captured by the driver monitoring camera 1.

In S14, the ECU 10 causes the eye state determination unit 12 to determine whether the eyelid opening of a driver is greater than or equal to the opening threshold value. If it is determined that the eyelid opening of the driver is greater than or equal to the opening threshold value (S14: YES), in S15, the eye state determination unit 12 determines that a state of an eye of the driver is an eye open state. If it is determined that the eyelid opening of the driver is less than the opening threshold value (S14: NO), in S16, the eye state determination unit 12 determines that a state of the eye of the driver is an eye closed state.

In S17, the ECU 10 causes the period calculation unit 14 to calculate an eye open period. The period calculation unit 14 calculates the eye open period based on a determination result output from the eye state determination unit 12.

In S18, the ECU 10 causes the notification control unit 15 to control a notification to the driver. For example, the notification control unit 15 calculates a time interval of blinks based on the eye open period calculated by the period calculation unit 14, and the notification control unit 15 determines that the alertness of the driver is diminishing if the time interval of blinks is less than the predetermined blink interval threshold value. If it is determined that the alertness of the driver is diminishing, the notification control unit 15 encourages the driver to take a rest by notifying the driver via voice, for example. Thereafter, the ECU 10 ends the computational process of FIG. 4.

Figure 5:
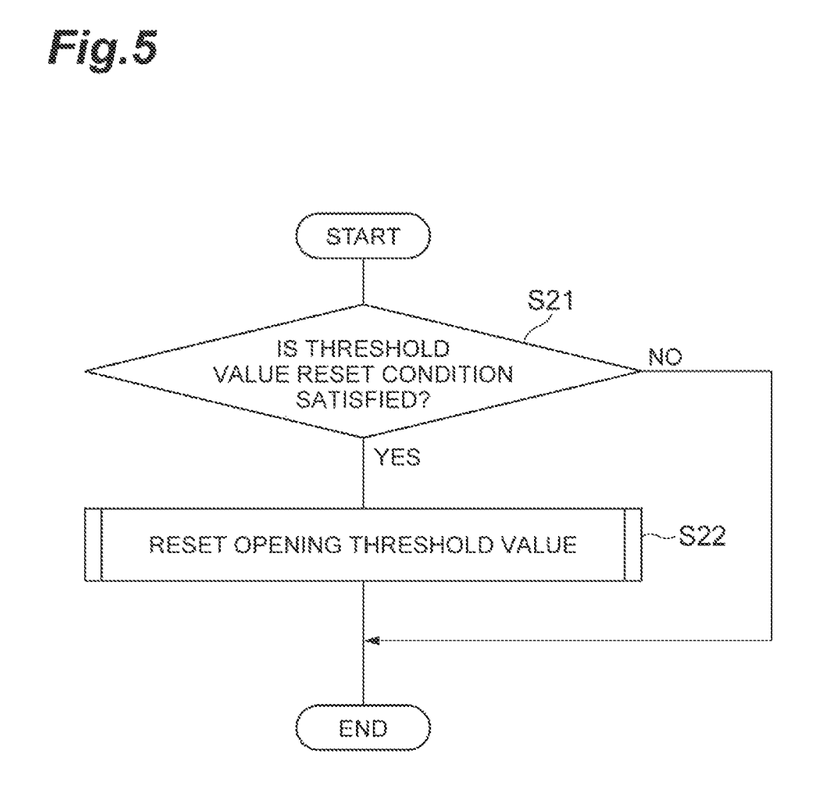
FIG. 5 is a flowchart illustrating a determination process of the first threshold value resetting.

Consecutively, FIG. 5 is a flowchart illustrating a determination process of the first threshold value resetting. The process of the flowchart illustrated in FIG. 5 is executed in parallel with the process of FIG. 4, for example, while the process of FIG. 4 is being executed.

In S21, the ECU 10 causes the threshold value resetting unit 13 to determine whether a threshold value reset condition has been satisfied. If it is determined that the threshold value reset condition has been satisfied (S21: YES), the threshold value resetting unit 13 resets the opening threshold value in S22. If it is determined that the threshold value reset condition has not been satisfied (S21: NO), the threshold value resetting unit 13 does not reset the opening threshold value. Thereafter, the ECU 10 ends the computational process of FIG. 5.

Figure 6:
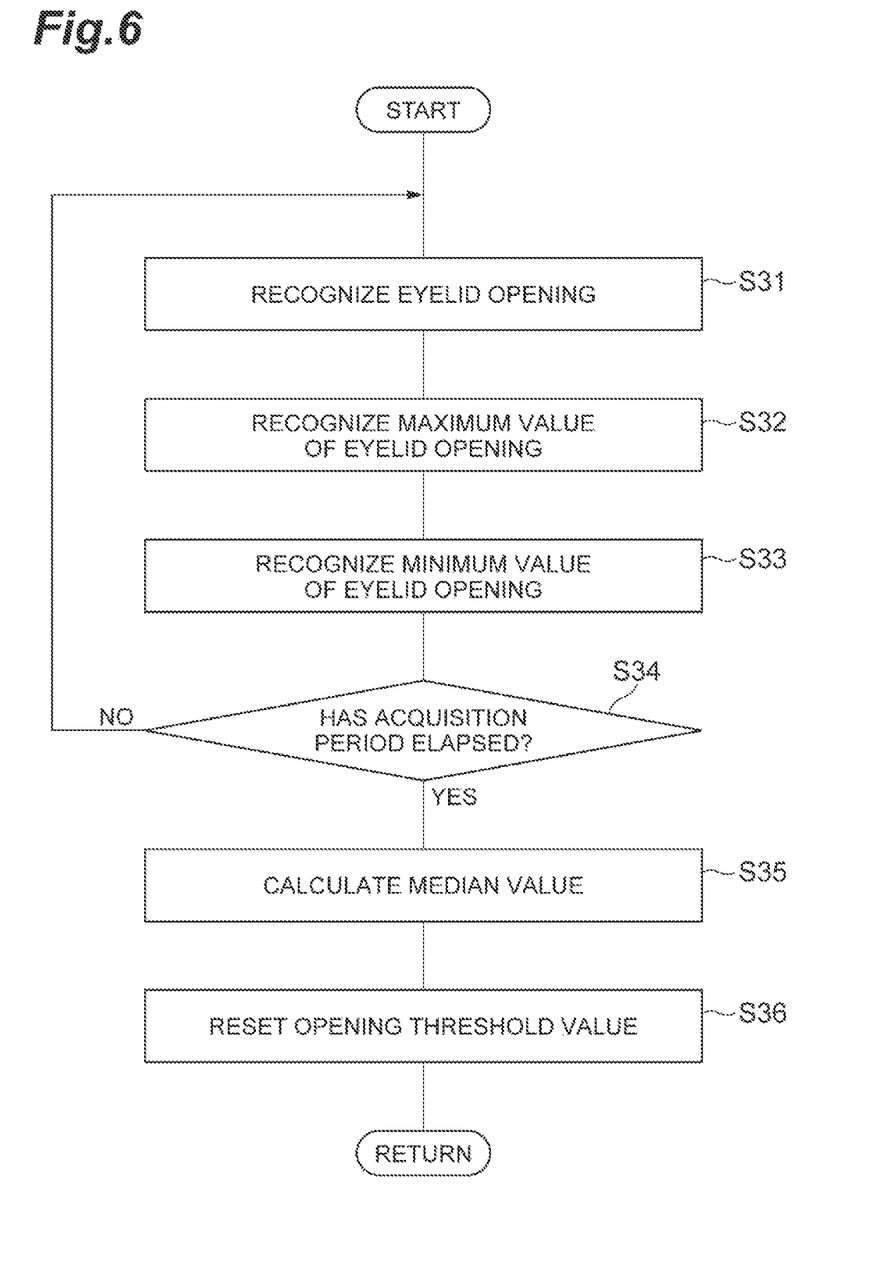
FIG. 6 is a flowchart illustrating a resetting process of the first threshold value resetting.

Specifically, the ECU 10 causes the eyelid opening recognition unit 11 and the threshold value resetting unit 13 to execute the process of FIG. 6, which is the step of resetting the opening threshold value in S22. FIG. 6 is a flowchart illustrating the resetting process of the first threshold value resetting.

In S31, the ECU 10 causes the eyelid opening recognition unit 11 to recognize an eyelid opening. The eyelid opening recognition unit 11 recognizes the eyelid opening based on image information captured by the driver monitoring camera 1. In S32, the ECU 10 causes the eyelid opening recognition unit 11 to recognize a maximum value of the eyelid opening. The eyelid opening recognition unit 11 recognizes the maximum value of the eyelid opening of the driver based on a calculated eyelid distance. In S33, the ECU 10 causes the eyelid opening recognition unit 11 to recognize a minimum value of the eyelid opening. The eyelid opening recognition unit 11 recognizes the minimum value of the eyelid opening based on the calculated eyelid distance.

In S34, the ECU 10 causes the threshold value resetting unit 13 to determine whether an acquisition period has elapsed. If the threshold value resetting unit 13 determines that the acquisition period has not elapsed (S34: NO), the ECU 10 transitions to S31, and repeats the steps in S31 to S33. If the threshold value resetting unit 13 determines that the acquisition period has elapsed (S34: YES), the ECU 10 causes the threshold value resetting unit 13 to calculate a median value in S35. The threshold value resetting unit 13 calculates a median value between the maximum value and the minimum value of the eyelid opening of the driver recognized by the eyelid opening recognition unit 11.

In S36, the ECU 10 causes the threshold value resetting unit 13 to reset the opening threshold value. The threshold value resetting unit 13 resets the opening threshold value to the calculated median value. Thereafter, the ECU 10 ends the computational process of FIG. 6.

In the occupant state recognition apparatus 100 described above, the threshold value resetting unit 13 resets the opening threshold value to a value between the maximum value and the minimum value of the eyelid opening of the driver recognized by the eyelid opening recognition unit 11, if the minimum value of the eyelid opening has not become less than or equal to the opening threshold value for the predetermined period or the period corresponding to the predetermined number of times of eyelid opening and closing (in other words, if the eye closed state has become the half-eye state). The eye state determination unit 12 can determine whether the eye is in the eye open state or the eye closed state because the opening threshold value is reset to the value between the maximum value and the minimum value of the eyelid opening of the driver. Therefore, the occupant state recognition apparatus 100 can properly recognize the state of the occupant by determining whether the eye is in the eye open state or the eye closed state while taking account of the individual differences.

Second Threshold Value Resetting

Subsequently, a second threshold value resetting operation and a second threshold value resetting process executed by the threshold value resetting unit 13 will be described with reference to FIGS. 7 and 8.

As a condition to initiate the second threshold value resetting, the threshold value resetting unit 13 determines whether there has been a driver replacement. The threshold value resetting unit 13 determines whether there has been a driver replacement, when based on a determination as to the possibility that the driver sitting in the driver's seat of the vehicle is replaced with another driver. The driver replacement does not necessarily require the driver to be actually replaced with another driver.

The threshold value resetting unit 13 may determine that there has been a driver replacement if it is determined that a driver's door in a closed state has been open, for example, when based on a detection result output from an opening and closing sensor of the driver's door. The threshold value resetting unit 13 may determine that there has been a driver replacement if it is determined that a current has been output, for example, when based on the current output to a courtesy lamp of the driver's door. The threshold value resetting unit 13 may determine that there has been a driver replacement if it is determined that a seatbelt of the driver's seat in a buckled state has been unbuckled, for example, when based on a detection result output from a seatbelt sensor of the driver's seat.

If the threshold value resetting unit 13 determined that there has been the driver replacement, the threshold value resetting unit 13 resets the opening threshold value to a value between the maximum value and the minimum value of the eyelid opening of the driver recognized by the eyelid opening recognition unit 11.

Figure 7:
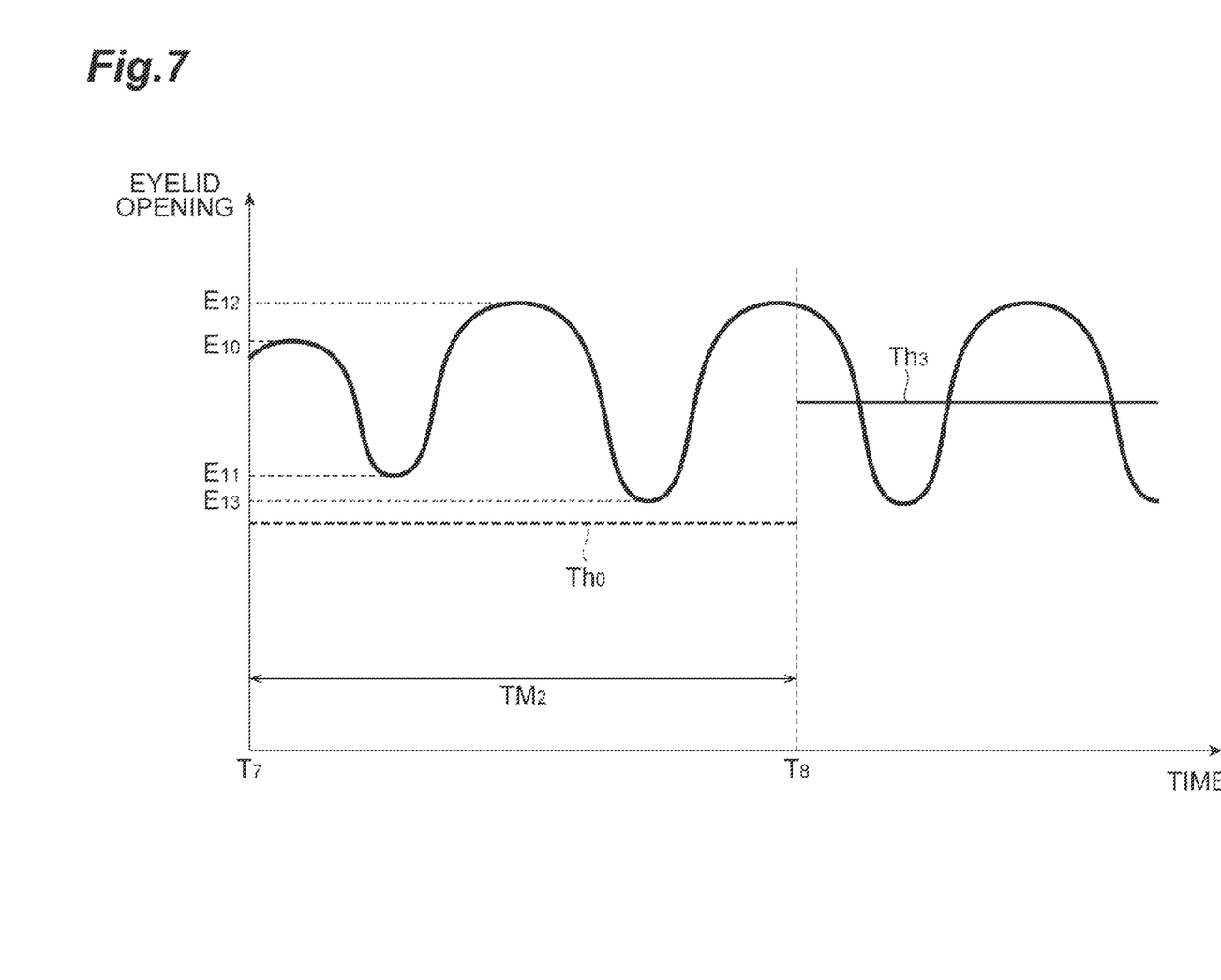
FIG. 7 is a timing chart illustrating an example of a second threshold value resetting.
Figure 8:
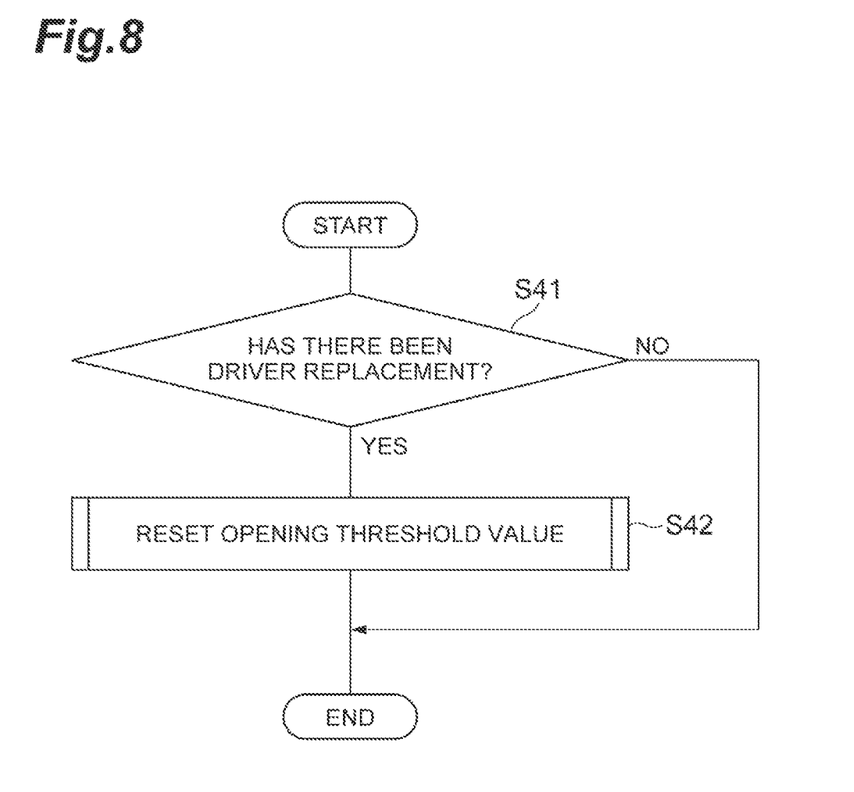
FIG. 8 is a flowchart illustrating a determination process of the second threshold value resetting.

FIG. 7 is a timing chart illustrating an example of the second threshold value resetting. In FIG. 7, the horizontal axis represents time. In FIG. 7, the vertical axis represents the eyelid opening. In FIG. 7, the solid line represents a change over time in the eyelid opening of the driver. As an example, FIG. 7 illustrates a case where the eye closed state becomes the half-eye state when the threshold value resetting unit 13 determined that there has been a driver replacement.

In FIG. 7, a time $T_7$ indicates the time at which the threshold value resetting unit 13 determines that there has been the driver replacement. In this case, the threshold value resetting unit 13 resets the opening threshold value to a value between a maximum value and a minimum value of the eyelid opening of the driver recognized by the eyelid opening recognition unit 11.

A time $T_8$ indicates the time that the period $TM_2$ (acquisition period described above) has elapsed from the time $T_7$. In the acquisition period from the time $T_7$ to the time $T_8$, the eyelid opening recognition unit 11 recognizes the maximum value and the minimum value of the eyelid opening of the driver. In the example illustrated in FIG. 7, firstly, the eyelid opening recognition unit 11 recognizes an eyelid opening $E_{10}$ as the maximum value of the eyelid opening of the driver in the period from the time $T_7$ to the time $T_8$. Subsequently, the eyelid opening recognition unit 11 recognizes an eyelid opening $E_{11}$ as the minimum value of the eyelid opening of the driver. Subsequently, the eyelid opening recognition unit 11 recognizes an eyelid opening $E_{12}$ as a new maximum value of the eyelid opening of the driver. Subsequently, the eyelid opening recognition unit 11 recognizes an eyelid opening $E_{13}$ as a new minimum value of the eyelid opening of the driver.

At the time $T_8$, the threshold value resetting unit 13 resets an opening threshold value $Th_3$ to a value between the eyelid opening $E_{12}$ recognized as the maximum value of the eyelid opening of the driver and the eyelid opening $E_{13}$ recognized as the minimum value of the eyelid opening of the driver. As the reset opening threshold value, the threshold value resetting unit 13 calculates a median value between the maximum value (eyelid opening $E_{12}$) and the minimum value (eyelid opening $E_{13}$), and resets the opening threshold value $Th_3$ to the median value. Therefore, after the time $T_5$, the eye state determination unit 12 can determine whether the eye is in the eye open state or the eye closed state.

Subsequently, the second threshold value resetting operation and the second threshold value resetting process executed by the threshold value resetting unit 13 will be described with reference to FIG. 8. FIG. 8 is a flowchart illustrating a determination process of the second threshold value resetting. The process of the flowchart illustrated in FIG. 8 is executed in parallel with the process of FIG. 4 while the process of FIG. 4 is being executed, for example.

In S41, the ECU 10 causes the threshold value resetting unit 13 to determine whether there has been a driver replacement. If the threshold value resetting unit 13 determined that there has been the driver replacement (S41: YES), the threshold value resetting unit 13 resets the opening threshold value in S42. Specifically, the ECU 10 enables the eyelid opening recognition unit 11 and the threshold value resetting unit 13 to execute the same process as in FIG. 6, which is the step of resetting the opening threshold value in S42. If the threshold value resetting unit 13 determined that there has been no driver replacement (S41: NO), the threshold value resetting unit 13 does not reset the opening threshold value. Thereafter, the ECU 10 ends the computational process of FIG. 8.

In the occupant state recognition apparatus 100 described above, the threshold value resetting unit 13 determines whether there has been a driver replacement, and if the threshold value resetting unit 13 determined that there has been the driver replacement, the threshold value resetting unit 13 resets the opening threshold value to a value between the maximum value and the minimum value of the eyelid opening of the driver recognized by the eyelid opening recognition unit 11. Therefore, the eye state determination unit 12 can certainly determine whether an eye is in the eye open state or the eye closed state, even though, for example, there are individual differences in the degree of eyelid opening and closing between the driver before the replacement and another driver after the replacement, because the opening threshold value is reset in association with the replacement.

Modification Example

The present disclosure is not limited to the embodiment. In addition to the embodiment, the present disclosure can be realized in various forms, to which modifications and improvements are made based on the knowledge of those skilled in the art.

Figure 9:
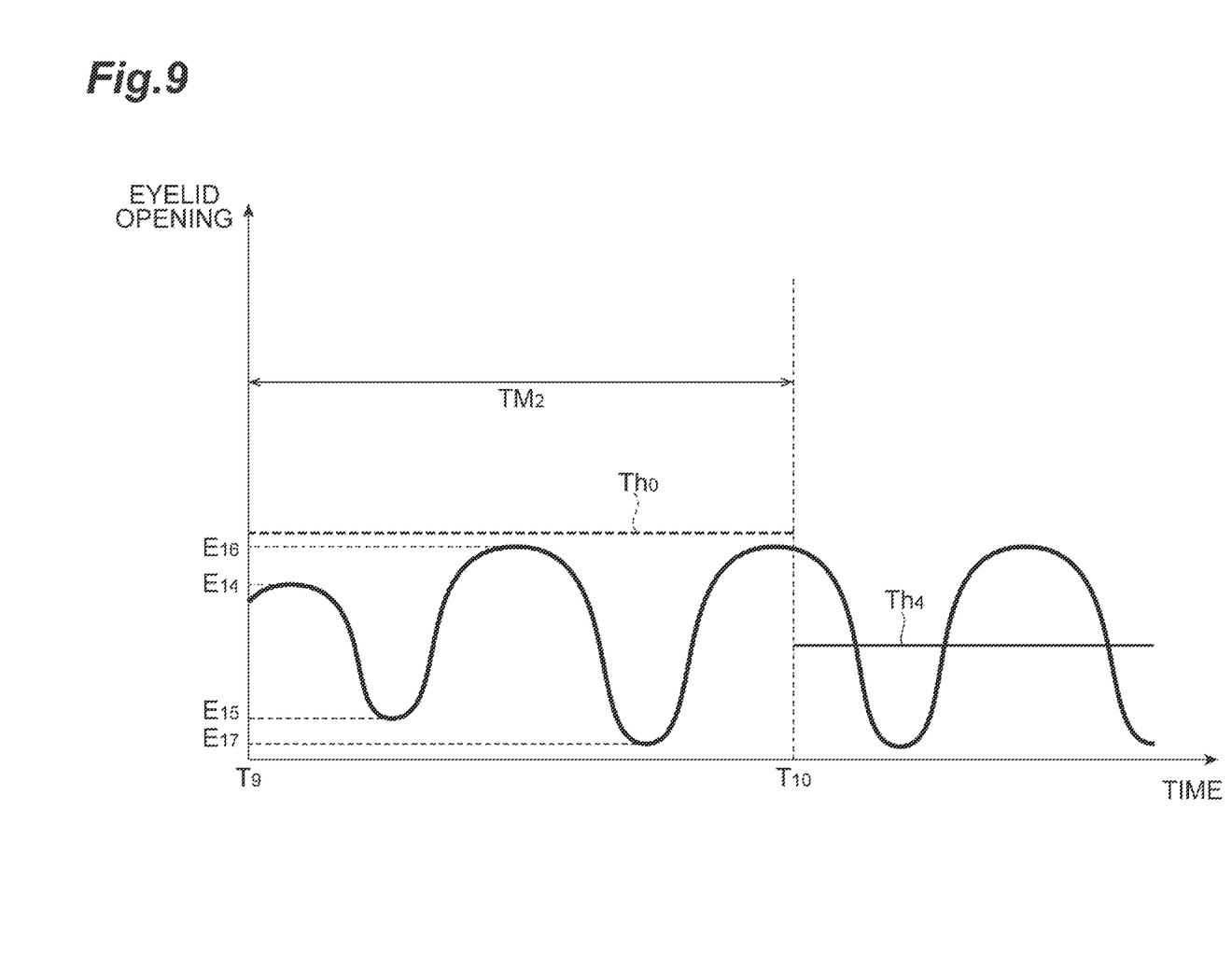
FIG. 9 is another timing chart illustrating an example of the second threshold value resetting.

As illustrated in FIGS. 2, 3, and 7, the embodiment exemplifies that the minimum value of the eyelid opening has not become less than or equal to the opening threshold value (the eye closed state has become the half-eye state); however, as illustrated in FIG. 9, the threshold value resetting unit 13 can reset the opening threshold value, even if the maximum value of the eyelid opening has not become greater than or equal to the opening threshold value (the eye open state has become the half-eye state).

FIG. 9 is another timing chart illustrating an example of the second threshold value resetting. The horizontal axis and the vertical axis of FIG. 9 represents the same parameters as the horizontal axis and the vertical axis of FIG. 7. As an example, FIG. 9 illustrates a case where the eye open state becomes the half-eye state when the threshold value resetting unit 13 determined that there has been a driver replacement.

In FIG. 9, a time $T_9$ indicates the time at which the threshold value resetting unit 13 determines that there has been the driver replacement. In this case, the threshold value resetting unit 13 resets the opening threshold value to a value between a maximum value and a minimum value of the eyelid opening of the driver recognized by the eyelid opening recognition unit 11.

A time $T_{10}$ indicates the time that the period $TM_2$ (acquisition period described above) has elapsed from the time $T_9$. The eyelid opening recognition unit 11 recognizes the maximum value and the minimum value of the eyelid opening of the driver in the acquisition period from the time $T_9$ to the time $T_{10}$. In the example illustrated in FIG. 9, firstly, the eyelid opening recognition unit 11 recognizes an eyelid opening $E_{14}$ as the maximum value of the eyelid opening of the driver in the period from the time $T_9$ to the time $T_{10}$. Subsequently, the eyelid opening recognition unit 11 recognizes an eyelid opening $E_{15}$ as the minimum value of the eyelid opening of the driver. Subsequently, the eyelid opening recognition unit 11 recognizes an eyelid opening $E_{16}$ as a new maximum value of the eyelid opening of the driver. Subsequently, the eyelid opening recognition unit 11 recognizes an eyelid opening $E_{17}$ as a new minimum value of the eyelid opening of the driver.

At the time $T_{10}$, the threshold value resetting unit 13 resets an opening threshold value $Th_4$ to a value between the eyelid opening $E_{16}$ recognized as the maximum value of the eyelid opening of the driver and the eyelid opening $E_{17}$ recognized as the minimum value of the eyelid opening of the driver. As the reset opening threshold value, the threshold value resetting unit 13 calculates a median value between the maximum value (eyelid opening $E_{16}$) and the minimum value (eyelid opening $E_{17}$), and resets the opening threshold value $Th_4$ to the median value. Therefore, after the time $T_0$, the eye state determination unit 12 can determine whether the eye is in the eye open state or the eye closed state.

The threshold value resetting unit 13 may reset the opening threshold value to the value between the maximum value and the minimum value of the eyelid opening of the driver recognized by the eyelid opening recognition unit 11 if the maximum value of the eyelid opening has not become greater than or equal to the opening threshold value (for example, opening threshold value $Th_0$) for the predetermined period (for example, period $TM_1$).

The threshold value resetting unit 13 may reset the opening threshold value to the value between the maximum value and the minimum value of the eyelid opening of the driver recognized by the eyelid opening recognition unit 11 if the maximum value of the eyelid opening has not become greater than or equal to the opening threshold value (for example, opening threshold value $Th_0$) for the period (for example, period TN) corresponding to the predetermined number of times of eyelid opening and closing. The number of times of eyelid opening and closing may increase, for example, at timings that the eyelid opening turns from increasing to decreasing while remaining less than the opening threshold value $Th_0$. Alternatively, the number of times of eyelid opening and closing may increase at timings that the eyelid opening turns from decreasing to increasing while remaining less than the opening threshold value $Th_0$.

Therefore, even though the maximum value of the eyelid opening has not become greater than or equal to the opening threshold value for the period corresponding to the predetermined number of times of eyelid opening and closing (even though the eye open state has become the half-eye state), the threshold value resetting unit 13 resets the opening threshold value to a value between the maximum value and the minimum value of the eyelid opening of the driver recognized by the eyelid opening recognition unit 11. Because the opening threshold value is reset to the value between the maximum value and the minimum value of the eyelid opening of the driver, the eye state determination unit 12 can determine whether the eye is in the eye open state or the eye closed state.

In the embodiment, the threshold value resetting unit 13 calculates a median value between the maximum value and the minimum value of the eyelid opening of the driver recognized by the eyelid opening recognition unit 11, and resets the opening threshold value to the median value; however, for example, the opening threshold value may be set based on only one of the maximum value and the minimum value. For example, if the minimum value of the eyelid opening has not become less than or equal to the opening threshold value for the predetermined period or the period corresponding to the predetermined number of times of eyelid opening and closing, only based on the minimum value, the threshold value resetting unit 13 may reset the opening threshold value to an eyelid opening obtained by adding a predetermined value to the minimum value, which is an opening between the maximum value and the minimum value. If the maximum value of the eyelid opening has not become greater than or equal to the opening threshold value for the predetermined period or the period corresponding to the predetermined number of times of eyelid opening and closing, only based on the maximum value, the threshold value resetting unit 13 may reset the opening threshold value to an eyelid opening obtained by subtracting a predetermined value to the maximum value, which is an opening between the maximum value and the minimum value.

In the embodiment, the eyelid opening recognition unit 11 calculates the 3-D distance from the upper eyelid to the lower eyelid as the eyelid distance to recognize the eyelid opening; however, the present disclosure is not limited to the embodiment. For example, as the eyelid distance, the eyelid opening recognition unit 11 may calculate a distance from the upper eyelid to the lower eyelid in a captured image of the eye of the driver captured by the driver monitoring camera 1. Alternatively, the eyelid opening recognition unit 11 may calculate an area ratio which is the ratio of an area of a white part of the eye to an area of a black part of the eye in the captured image of the eye of the driver captured by the driver monitoring camera 1, and recognize the area ratio as the eyelid opening.

In the embodiment, a ratio between the eyelid distance calculated by the eyelid opening recognition unit 11 and the maximum eyelid distance, that is, a maximum value of the eyelid distance is exemplified as the eyelid opening; however, the eyelid distance calculated by the eyelid opening recognition unit 11 may be used as the eyelid opening.

In the embodiment, the notification control unit 15 notifies the driver via voice if it is determined that the alertness of the driver is diminishing; however, for example, the notification control unit 15 may notify the driver by vibrating the seat, or may not necessarily notify the driver. The notification control unit 15 may be omitted.

In the example (the eye closed state has become the half-eye state) of the embodiment illustrated in FIG. 3, the number of times of eyelid opening and closing increases at the timings that the eyelid opening turns from decreasing to increasing while remaining greater than the opening threshold value $Th_0$; however, the number of times of eyelid opening and closing may increase at the timings that the eyelid opening turns from increasing to decreasing while remaining greater than the opening threshold value $Th_0$.

In the embodiment, the period calculation unit 14 calculates the eye open period which is a period from when the eye has entered the eye open state to when the eye has entered the eye closed state based on the determination result output from the eye state determination unit 12; however, the period calculation unit 14 may calculate the eye closed period which is a period from when the eye has entered the eye closed state to when the eye has entered the eye open state.

In the embodiment, the occupant state recognition apparatus 100 can execute the second threshold value resetting in addition to the first threshold value resetting; however, the occupant state recognition apparatus 100 may execute at least one of the first threshold value resetting and the second threshold value resetting.

In the embodiment, the threshold value resetting unit 13 may be prohibited from further resetting the opening threshold value if the opening threshold value has been once reset, until a predetermined condition is satisfied. The predetermined condition may indicate a condition where the threshold value resetting unit 13 determines that there has been a driver replacement, for example. In this case, it is possible to avoid the possibility that the eyelid opening threshold value is excessively reset several times even though there has been no driver replacement.

What is claimed is:

1. An occupant state recognition apparatus that recognizes a state of an occupant by determining an eye open state and an eye closed state of an eye of a driver sitting in a driver's seat of a vehicle, the apparatus comprising:
    an eyelid opening recognition unit configured to recognize an eyelid opening of the driver, a maximum value of the eyelid opening of the driver, and a minimum value of the eyelid opening of the driver based on image information captured by a driver monitoring camera of the vehicle;
    an eye state determination unit configured to determine that the eye is in the eye open state if the eyelid opening becomes greater than or equal to a threshold value which is preset, and to determine that the eye is in the eye closed state if the eyelid opening becomes less than the threshold value; and
    a threshold value resetting unit configured to reset the threshold value to a value between the maximum value and the minimum value of the eyelid opening of the driver recognized by the eyelid opening recognition unit, if the maximum value has not become greater than or equal to the threshold value for a period corresponding to a predetermined number of times of eyelid opening and closing, or if the minimum value has not become less than or equal to the threshold value for the period corresponding to the predetermined number of times of eyelid opening and closing.

2. An occupant state recognition apparatus that recognizes a state of an occupant by determining an eye open state and an eye closed state of an eye of a driver sitting in a driver's seat of a vehicle, the apparatus comprising:
    an eyelid opening recognition unit configured to recognize an eyelid opening of the driver, a maximum value of the eyelid opening of the driver, and a minimum value of the eyelid opening of the driver based on image information captured by a driver monitoring camera of the vehicle;
    an eye state determination unit configured to determine that the eye is in the eye open state if the eyelid opening becomes greater than or equal to a threshold value which is preset, and to determine that the eye is in the eye closed state if the eyelid opening becomes less than the threshold value; and
    a threshold value resetting unit configured to reset the threshold value to a value between the maximum value and the minimum value of the eyelid opening of the driver recognized by the eyelid opening recognition unit, if the maximum value has not become greater than or equal to the threshold value for a predetermined period or a period corresponding to a predetermined number of times of eyelid opening and closing, or if the minimum value has not become less than or equal to the threshold value for the predetermined period or the period corresponding to the predetermined number of times of eyelid opening and closing,
    wherein the threshold value resetting unit is configured to determine whether there has been a driver replacement, and to reset the threshold value to the value between the maximum value and the minimum value of the eyelid opening of the driver recognized by the eyelid opening recognition unit, if the threshold value resetting unit determined that there has been the driver replacement.

3. The occupant state recognition apparatus according to claim 1, further comprising:
    a notification control unit configured to control a notification to the driver based on a time interval of blinks calculated based on an eye open period, and to notify the driver if the time interval of blinks is less than a predetermined blink interval threshold value.

4. The occupant state recognition apparatus according to claim 2, further comprising:
    a notification control unit configured to control a notification to the driver based on a time interval of blinks calculated based on an eye open period, and to notify the driver if the time interval of blinks is less than a predetermined blink interval threshold value.

* * * * *